US007957502B2

(12) United States Patent
Manabe et al.

(10) Patent No.: US 7,957,502 B2
(45) Date of Patent: Jun. 7, 2011

(54) METHOD FOR SCALING SCATTERED RAY INTENSITY DISTRIBUTION IN MULTI BULBS X-RAY CT AND MULTI BULBS X-RAY CT APPARATUS

(75) Inventors: Takahiro Manabe, Kanagawa-ken (JP); Naruomi Akino, Tochigi-ken (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 330 days.

(21) Appl. No.: 12/243,218

(22) Filed: Oct. 1, 2008

(65) Prior Publication Data
US 2009/0092221 A1    Apr. 9, 2009

(30) Foreign Application Priority Data

Oct. 2, 2007   (JP) ................................ 2007-258988

(51) Int. Cl.
*G01N 23/00*    (2006.01)
(52) U.S. Cl. ......... 378/7; 378/6; 378/9; 378/86; 378/87; 378/92
(58) Field of Classification Search ................. 378/6, 7, 378/9, 86, 87
See application file for complete search history.

(56) References Cited

U.S. PATENT DOCUMENTS

| | | | | |
|---|---|---|---|---|
| 6,876,719 | B2 * | 4/2005 | Ozaki | 378/7 |
| 6,980,626 | B2 * | 12/2005 | Groh et al. | 378/87 |
| 7,145,980 | B2 * | 12/2006 | Sakaguchi et al. | 378/7 |
| 7,440,536 | B2 * | 10/2008 | Bruder et al. | 378/7 |

(Continued)

FOREIGN PATENT DOCUMENTS

JP        11-299768        11/1999

(Continued)

*Primary Examiner* — Hoon Song
*Assistant Examiner* — Mona M Sanei
(74) *Attorney, Agent, or Firm* — Oblon, Spivak, McClelland, Maier & Neustadt, L.L.P.

(57) ABSTRACT

A method for scaling a scattered ray intensity distribution in a multi bulbs X-ray CT apparatus configured to irradiate a subject with X-rays from a plurality of X-ray generation sections, respectively and configure a cross-sectional image of the subject by detecting the X-rays passing through the subject. A first difference is achieved, the first difference being the difference between a real data of X-ray intensity achieved by passing of X-rays through the subject, the X-rays being radiated from the plurality of the X-ray generation sections, respectively and an opposed data of X-ray intensity achieved by passing of these X-rays through the subject at the same position in an opposite direction, a second difference between scattered ray intensity included in the real data and scattered ray intensity included in the opposed data being achieved. Primary scattered ray included in the real data of the X-ray intensity achieved by passing of the X-rays through the subject, the X-rays being radiated from the plurality of the X-ray generation sections, respectively are estimated. Primary scattered ray included in the opposed data of the X-ray intensity achieved by passing of the X-rays through the subject at the same position in an opposite direction, respectively, and performing scaling the primary estimated scattered ray intensity distribution on the basis of a ratio between the first difference and the second difference are estimated.

20 Claims, 11 Drawing Sheets

U.S. PATENT DOCUMENTS

| | | | | |
|---|---|---|---|---|
| 7,443,945 | B2* | 10/2008 | Bruder et al. | 378/7 |
| 7,535,987 | B2* | 5/2009 | Matsuda | 378/7 |
| 7,609,803 | B2* | 10/2009 | Okamoto et al. | 378/7 |
| 7,623,617 | B2* | 11/2009 | Popescu | 378/7 |
| 7,660,381 | B2* | 2/2010 | Joosten et al. | 378/7 |
| 2007/0081622 | A1* | 4/2007 | Bruder et al. | 378/7 |

FOREIGN PATENT DOCUMENTS

| | | |
|---|---|---|
| JP | 2006-334319 | 12/2006 |
| JP | 2007-111314 | 5/2007 |

* cited by examiner

FIG. 4A
FIG. 4B
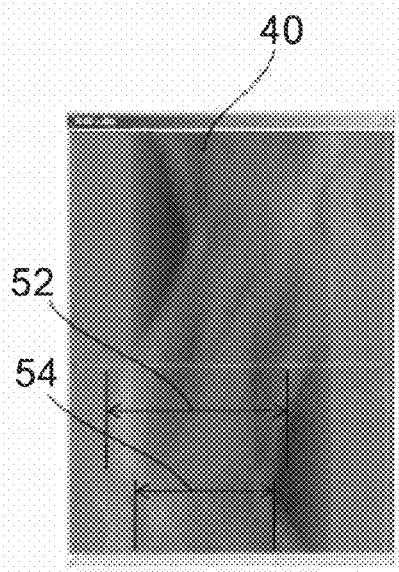
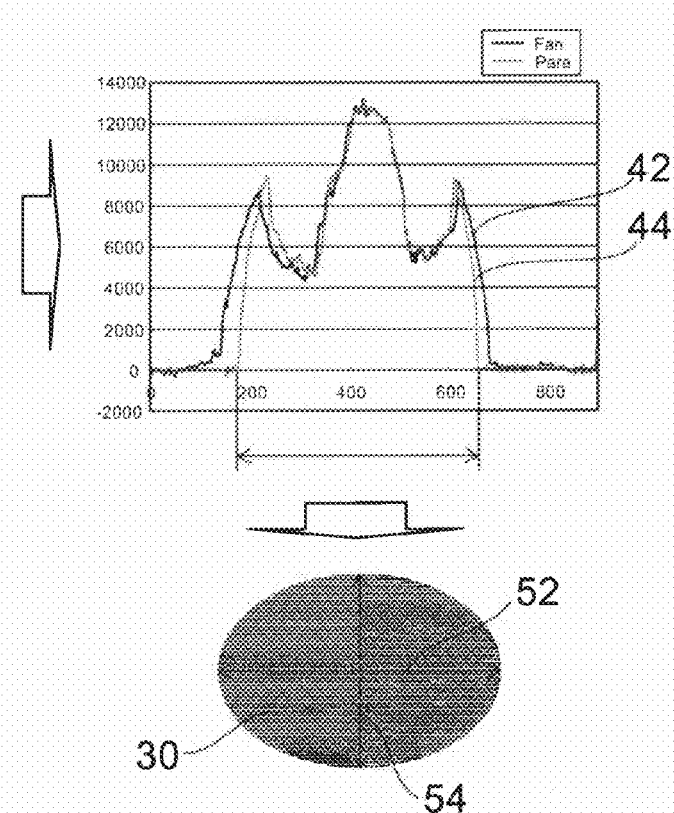

METHOD FOR SCALING SCATTERED RAY INTENSITY DISTRIBUTION IN MULTI BULBS X-RAY CT AND MULTI BULBS X-RAY CT APPARATUS

CROSS-REFERENCE TO RELATED APPLICATIONS

This application is based upon and claims the benefit of priority from the prior Japanese Patent Application No. 2007-258988, filed on Oct. 2, 2007; the entire contents of which are incorporated herein by reference.

BACKGROUND OF THE INVENTION

1. Field of the Invention

This invention relates to a method for scaling scattered ray intensity in multi bulbs X-ray CT by calculation from a detection signal and a multi bulbs X-ray CT apparatus.

2. Background Art

An X-ray CT apparatus detects intensity of X-rays (hereafter referred to as main ray) radiated from an X-ray bulb and going straight through a subject, and forms a cross-sectional image of the subject. At this time, detection of X-rays scattered from the subject (hereafter referred to as scattered ray) and the main ray produces a ghost image on the cross-sectional image resulting in degradation of image quality. Conventionally, the scattered ray incident from an oblique direction to a detector has been screened by placing a collimator beside the detector, but the scattered ray incident from normal to the detector has been unable to be separated. A technique simulating the scattered ray using a Monte Carlo method and removing the scattered ray component from an original signal configuring the image detected by the detector (e.g. JP-A 11-299768 (Kokai) (1999)) and a technique forming a correction data having the scattered component removed by simulation and configuring a high-precision image (e.g. JP-A 2006-334319 (Kokai)) are disclosed.

However, while a intensity distribution of the scattered ray can be estimated from a structure of the apparatus and a shape of the subject by simulating X-ray tracks by the Monte Carlo method, there has been a problem associated with taking a too long time for a purpose tracking only component incident to the detector to produce an error out of the scattered X-ray, because the Monte Carlo method tracks all scattering tracks. Therefore, application to subjects of all types of shapes has been difficult.

On the other hand, for the purpose of shortening measurement time and achieving a high resolution, in these years, an X-ray CT apparatus having multi bulbs has received attention. The multi bulbs X-ray CT apparatus has large effects produced by the scattered ray from other bulbs incident from normal to the detector, and the effects cannot be screened by the collimator. On the contrary, from viewpoint of possibility of improving degradation of image quality by calculating to correct only intensity of a primary scattered ray scattered once in the interior of the subject, the correction using a primary scattering estimation method has been considered to be effective, and a relative intensity distribution of the scattered rays on the detector can be estimated. However, the estimated scattered rays have relative intensity distribution, thus scaling is necessary for correcting really.

SUMMARY OF THE INVENTION

According to an aspect of the invention, there is provided a method for scaling a scattered ray intensity distribution in a multi bulbs X-ray CT apparatus configured to irradiate a subject with X-rays from a plurality of X-ray generation sections, respectively and configure a cross-sectional image of the subject by detecting the X-rays passing through the subject, the method including: a first difference being achieved, the first difference being the difference between a real data of X-ray intensity achieved by passing of X-rays through the subject, the X-rays being radiated from the plurality of the X-ray generation sections, respectively and an opposed data of X-ray intensity achieved by passing of these X-rays through the subject at the same position in an opposite direction, a second difference between scattered ray intensity included in the real data and scattered ray intensity included in the opposed data being achieved, the being achieved including: estimating a primary scattered ray included in the real data of the X-ray intensity achieved by passing of the X-rays through the subject, the X-rays being radiated from the plurality of the X-ray generation sections, respectively; and estimating a primary scattered ray included in the opposed data of the X-ray intensity achieved by passing of the X-rays through the subject at the same position in an opposite direction, respectively, and performing scaling the estimated primary scattered ray intensity distribution on the basis of a ratio between the first difference and the second difference.

According to another aspect of the invention, there is provided a multi bulbs X-ray CT apparatus including: a plurality of X-ray generation sections configured to generate X-rays; an X-ray detection section configured to detect the X-rays passing through a subject; an image reconfiguration section configured to configure a cross-sectional image of the subject on the basis of results detected by the X-ray detection section; and a scattered ray calculation section configured to estimate a primary scattered ray intensity distribution of the X-rays in the subject, the scattered ray calculation section achieving a first difference between a real data of the X-ray intensity achieved on the X-ray detection section by passing of the X-rays through the subject, the X-rays being radiated from the plurality of the X-ray generation sections and an opposed data of the X-ray intensity achieved on the X-ray detection section by passing of these X-rays through the subject at the same position in an opposite direction, achieving a second difference between scattered ray intensity included in the real data and scattered ray intensity included in the opposed data, the achieving including: estimating primary scattered ray included in the real data of the X-ray intensity achieved by passing of the X-rays through the subject, the X-rays being radiated from the plurality of the X-ray generation sections; and estimating primary scattered ray included in the opposed data of the X-ray intensity achieved by passing of these X-rays through the subject at the same position in an opposite direction, and performing scaling the estimated primary scattered ray intensity distribution on the basis of a ratio between the first difference and the second difference, and the image reconfiguration section reconfiguring the cross-sectional image by correcting the results detected by the X-ray detection section using the primary scattered ray intensity distribution scaled by the scattered ray calculation section.

BRIEF DESCRIPTION OF THE DRAWINGS

FIGS. 4A and 4B are data views for describing an estimation procedure of an outer shape of the subject 30;

DETAILED DESCRIPTION OF THE INVENTION

An embodiment of the invention will now be described with reference to the drawings.

Figure 1:
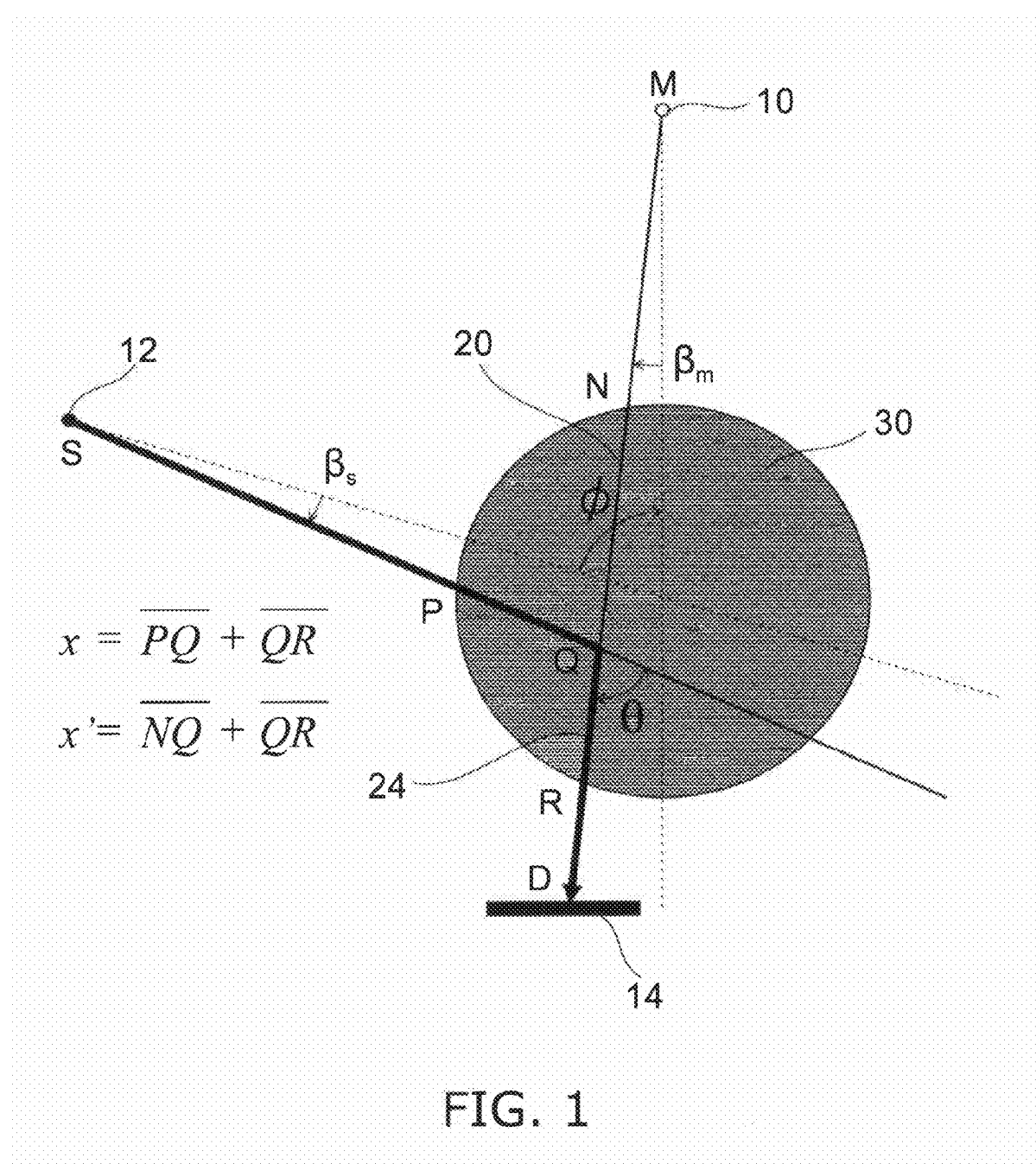
FIG. 1 is a schematic view describing a method for estimating a primary scattered ray intensity distribution according to the embodiment of the invention.

FIG. 1 is a schematic view describing a method for estimating a primary scattered ray intensity distribution according to the embodiment of the invention.

X-rays radiated from a first bulb (X-ray generation section) 10 located at a point M in a direction of an angle $\beta m$ with respect to a center of a subject 30 is incident to the subject 30 at a point N. A transmission ray 20 passes through the subject 30 along a path NQR to a point R via a point Q and reaches a detector 14 at a point D on the detector 14. A path length x' of the transmission ray 20 in the interior of the subject 30 is given by a following equation.

$$x'=NQ+QR$$

Here, in an X-ray CT, besides the first bulb 10, a second bulb 12 generating X-rays can be provided. Besides the transmission ray 20 from the first bulb 10, the X-rays radiated from the second bulb 12 located at a point S in a direction of an angle $\phi$ with respect to the first bulb 10 viewed from the subject 30 is also scattered in the interior of the subject 30 to reach the detector 14. That is, a source of the scattered ray includes illustratively scattering of the X-rays radiated from the second X-ray bulb 12 provided besides the first bulb 10. A specific example provided with the second bulb 12 will be described.

The X-rays radiated from the second bulb 12 in a direction of an angle $\beta s$ with respect to the center of the subject 30 is incident to the subject 30 at a point of P. A primary scattered ray 24 scattered once with a scattering angle $\theta$ at a point Q in the interior of the subject 30 passes through the subject 30 along a path PQR and reaches the detector 14 at the point D. A path length x of the primary scattered ray 24 is given by a following equation.

$$x=PQ+QR$$

The X-rays radially radiated from the second bulb 12 by varying $\beta s$ are scattered in the interior of the subject 30 and the scattered rays are integrated to calculate the intensity of the primary scattered ray 24 at the point D. While the second bulb 12 is placed imaginarily to calculate the intensity of the scattered ray, it is possible to place it really to collect experimental data and compare estimated values with experimental values.

Assuming the intensity of the transmission ray 20 to be Ip and the intensity of the primary scattered ray 24 to be Is, an X-ray intensity I at the point D on the detector 14 is given by a following equation.

$$I=Ip+\Sigma Is$$

Here, the first term in a right side of the above equation is the intensity of the transmission ray 20 on the detector 14, and the second term in the right side is the intensity of the primary scattered ray 24 on the detector 14. Furthermore, varying the angle $\beta s$ of the X-rays radiated from the first bulb 10 makes it possible to achieve the distribution of the primary scattered ray intensity $\Sigma Is$ and the distribution of the intensity Ip of the transmission ray 24 on the detector 14 while scanning the position of the detection point D on the detector 14, moreover the distribution of the X-ray intensity I can be achieved as the sum of them.

Figure 2:
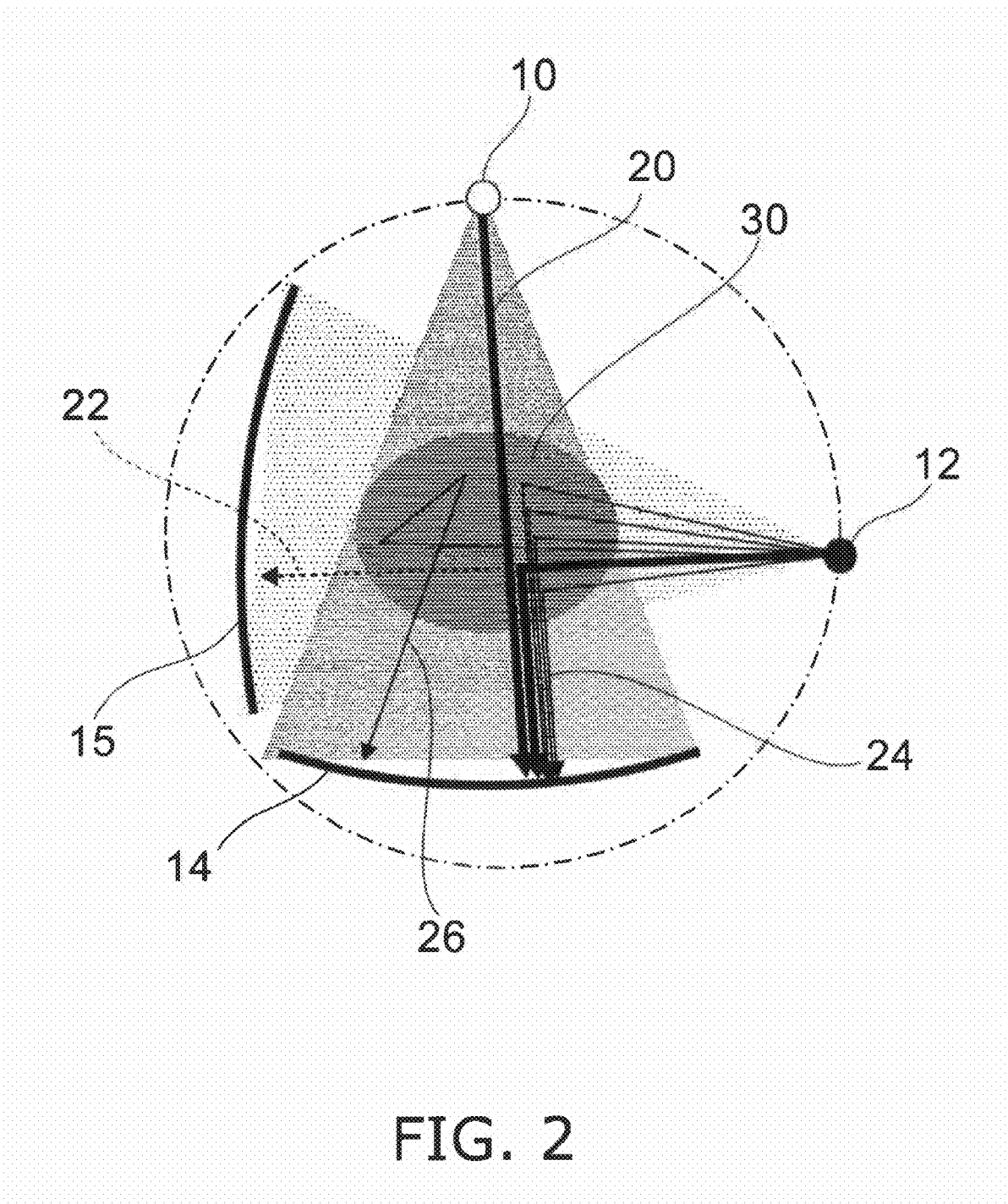
FIG. 2 is a schematic view describing scattering of X-rays in the interior of a subject.

FIG. 2 is a schematic view describing the scattering of X-rays in the interior of the subject 30.

The X-rays radiated radially from the second bulb 12 is scattered at every point in the subject 30 and reach the detector 14 as well as the transmission ray 24 from the first bulb 10. A multiply scattered ray 26 having a plurality of scatterings also reaches the detector 14. Assuming uniformity of a sectional structure of the subject 30 and neglecting the multiply scattered ray 26, an incident intensity distribution to the detector 14 is calculated for only the primary scattered ray 24 having only one scattering in the interior of the subject 30. Placing a detector 15 at a position opposite to the second bulb 12 also allows a transmission ray 22 from the second bulb 12 to be detected. It is noted that the subject 30 is assumed to be an elliptical shape to imitate a human body.

A calculation procedure of the scattered ray intensity distribution will be described.

Figure 3:
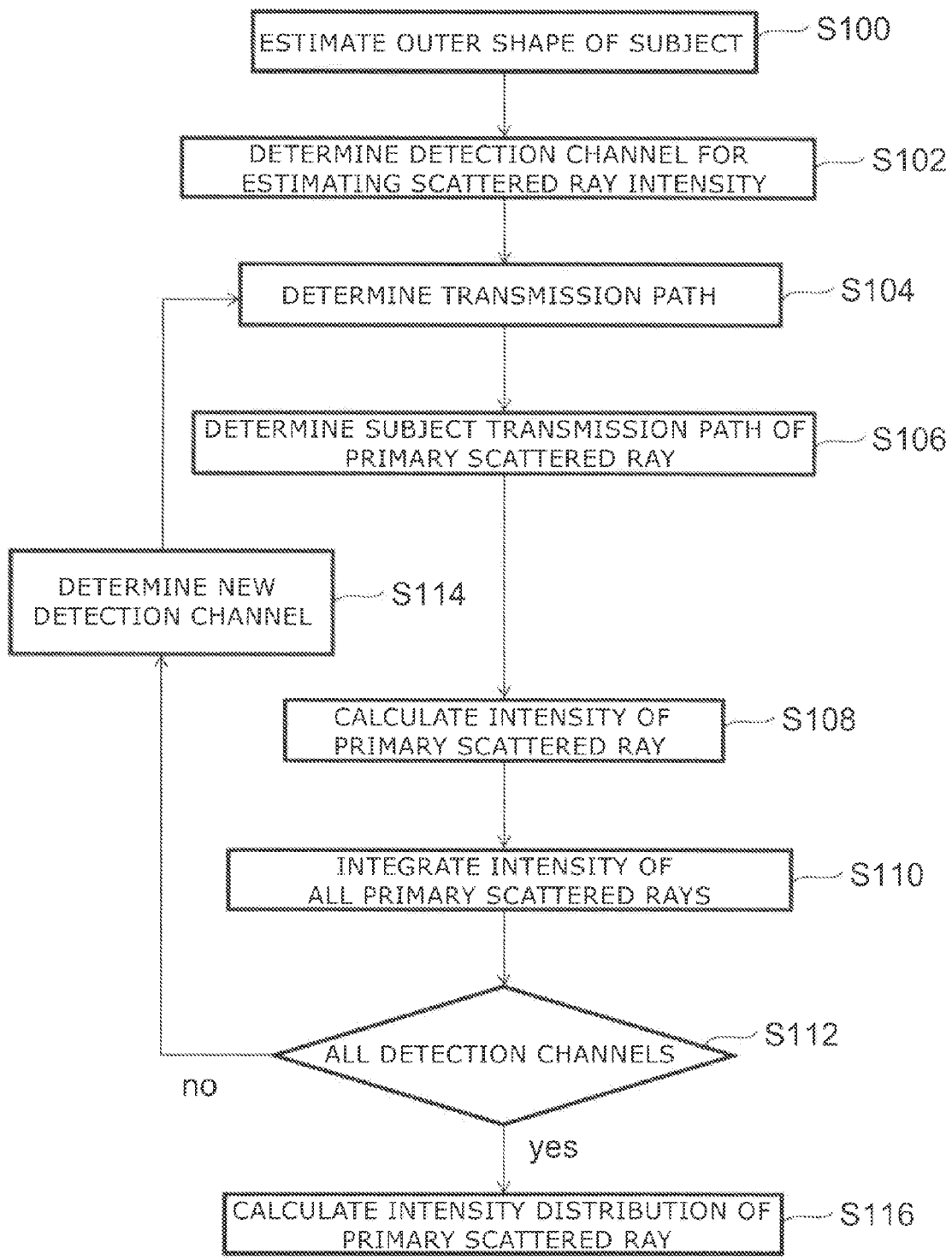
FIG. 3 is a flow chart illustrating a method for estimating the scattered ray intensity distribution of X-rays according to the embodiment of the invention.

FIG. 3 is a flow chart illustrating a method for estimating the scattered ray intensity distribution of the X-rays according to the embodiment of the invention.

The method for estimation of the embodiment includes estimating an outer shape of the subject (step S100), determining a detection channel for estimating the scattered ray intensity (step S102), determining a transmission path between the bulb and the detection channel (step S104), determining a subject transmission path of the primary scattered ray (step S106), calculating the intensity of the primary scattered ray (step S108), integrating the intensity of all primary scattered rays (step S110), judging whether integration of the primary scattered ray is performed or not for all detection channels (step S112), determining a new detection channel (step S114) and calculating the primary scattered ray intensity distribution on the detector (step S116).

FIGS. 4A and 4B are data views for describing an estimation procedure of the outer shape of the subject 30 (step S100).

As shown in FIG. 4A, a projection data 40 of the subject 30 including the scattered rays is obtained. Next, as shown in FIG. 4B, a profile along channels on the detector 14 is achieved from the projection data 40. A major axis profile 42 and a minor axis profile 44 achieved with reference to a major axis 52 and a minor axis 54 of the subject 30 imitating an elliptic body represent a intensity associating with light and dark of the projection data 40. The major axis 52 and the minor axis 54 can be achieved from widths of profiles respectively.

FIGS. 5A to 5D are schematic views describing an estimation procedure of the scattered ray intensity.

Figure 5A:
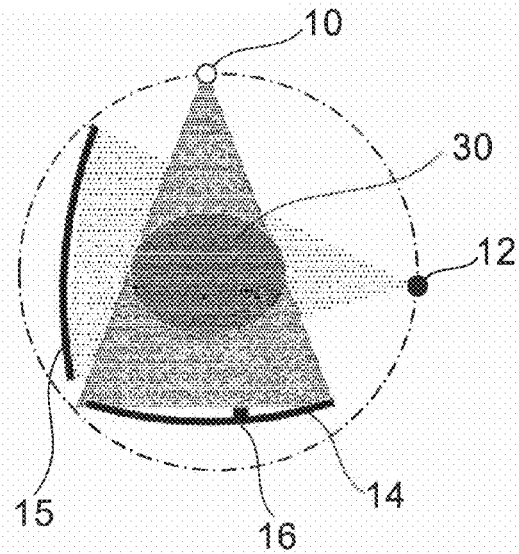
FIGS. 5A to 5D are schematic views describing an estimation procedure of scattered ray intensity.

FIG. 5A represents determining a detection channel 16 for estimating the scattered ray intensity (step S102) on the detector 14. The scattered ray intensity is estimated on each of all detection channels 16 arrayed on the detector 14, and the X-ray intensity distribution on the detector 14 is achieved by integrating them.

Figure 5B:
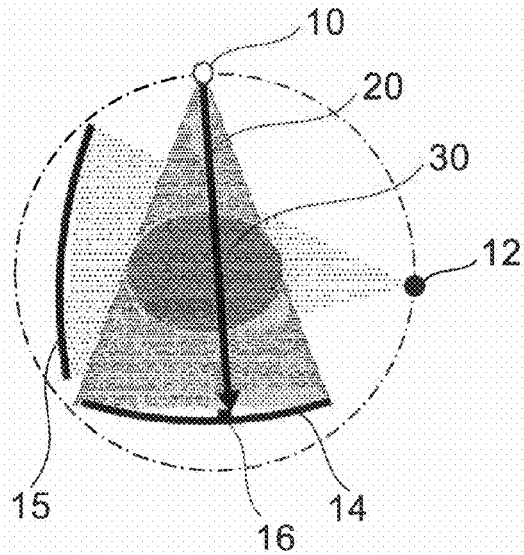

FIG. 5B represents determining the transmission path (step S104). Connecting the first bulb 10 and the detection channel 16 determines the transmission path of the X-rays to be detected. When the X-ray intensity radiated from the first bulb 10 is Io, assuming an X-ray absorption coefficient of the subject 30 to be μ and the transmission path length to be x' as shown in FIG. 1, the transmission ray intensity Ip to be detected by the detection channel 16 is given by a following equation.

$$Ip = Io \times \exp(-\mu x') \quad (1)$$

Figure 5C:
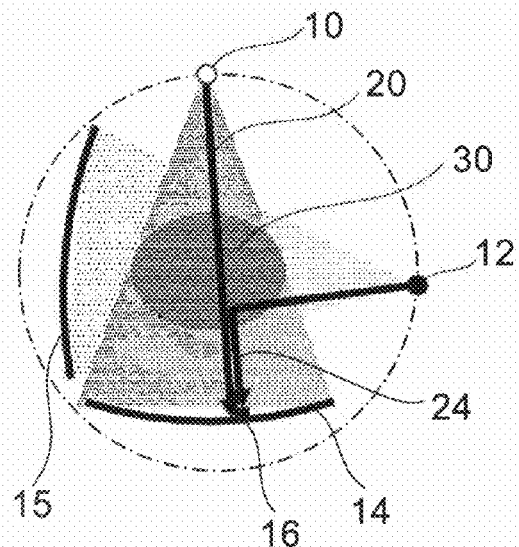

FIG. 5c represents determining the substrate transmission path of the primary scattered ray 24 (step S106) and calculating the intensity of the primary scattered ray 24 (step S108). Out of X-rays from the second bulb 12 provided imaginarily or experimentally, the transmission path of the primary scattered ray 24 having only one scattering in the interior of the subject 30 is achieved to calculate the scattered ray intensity Is to be detected by the detection channel 16. Assuming the X-ray intensity radiated from the second bulb 12 to be Io, the X-ray absorption coefficient of the subject 30 to be μ, the transmission path length to be x as shown in FIG. 1 and a scattering probability of X-ray to be P(θ), the scattered ray intensity Is is given by a following equation, $$Is = Io \times \exp(-\mu x) \times P(\theta) \quad (2)$$

where θ is a scattering angle of the primary scattered ray shown in FIG. 1.

Figure 5D:
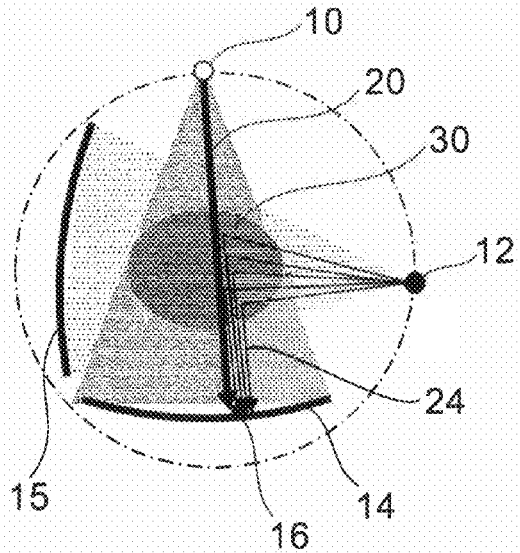

FIG. 5d represents integrating the intensity of all primary scattered rays 24 (step S110). As described above with reference to FIG. 1, the incidence angle βs of X-rays radiated from the second bulb 12 is, for example, varied every 0.1 degree and paths of all generated primary scattered rays are determined, and the scattered ray intensity Is of every primary scattered ray 24 to be detected by the channel 16 is integrated. At this time, the detection intensity I to be detected by the channel 16 is I=Ip+ΣIs.

As a result of estimating the primary scattering, ΣIs is achieved as the intensity of the estimated scattered rays.

As described above with reference to FIG. 1, performing from step S104 to step S110 for all detection channels 16 on the detector 14 while varying the angle βm of the X-rays radiated from the first bulb 10 allows the X-ray intensity distribution and the primary scattered ray intensity distribution on the detector 14 to be obtained.

Furthermore, reconfiguration of the projection data collected by rotating the first bulb 10 and the second bulb around the subject 30 enables a cross-sectional image (tomogram) to be obtained.

In the above description, attention has been paid to the scattering from another second bulb 12 other than the first bulb 10 with regard to the scattering in the interior of the subject 30. This is because the scattered ray from another second bulb 12 other than the first bulb 10 has been supposed as a scattered ray normally incident to the detector 14 unable to be removed by a collimator. However, removal of the scattering in the interior of the subject 30 of X-rays from the first bulb 10 is also a problem for the X-ray CT apparatus. Particularly, when the detection channel becomes smaller from the viewpoint of improving a resolution, difficulty of providing the collimator increases, and necessity for the X-ray CT apparatus without the collimator arises.

On the other hand, in the multi bulbs X-ray CT, removal of the scattered ray incident from normal to the detector becomes a problem. In that case, a method for removing the scattered ray from the first bulb 10 by calculation without use of devices provided on the apparatus is absolutely necessary.

Next, a second embodiment of the invention will be described.

Figure 6:
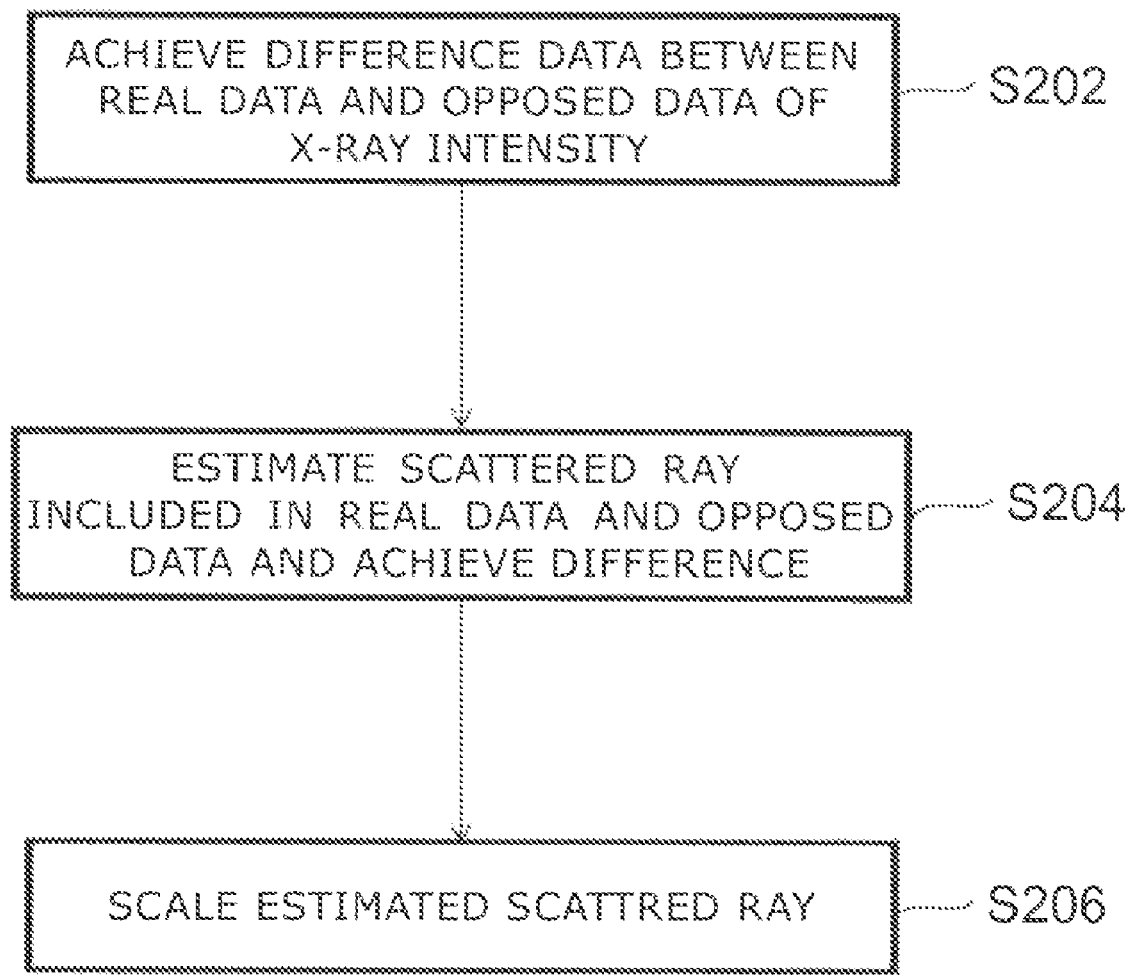
FIG. 6 is a flow chart illustrating a method for scaling of the scattered ray intensity distribution of the multi bulbs X-ray CT according to a second embodiment of the invention.

FIG. 6 is a flow chart illustrating a method for scaling of the scattered ray intensity distribution of the multi bulbs X-ray CT according to the second embodiment of the invention.

Here, 'scaling' corresponds to correction of the estimated primary scattered ray intensity.

The method for scaling the scattered ray intensity of this embodiment includes differentiating a real data and an opposed data of the X-ray intensity (step S202), estimating the scattered ray included in the real data and the scattered ray included in the opposed data and differentiating these scattered rays (step S204), and scaling the estimated scattered ray using peak values of two difference data (step S206).

Figures 7A, 7B:
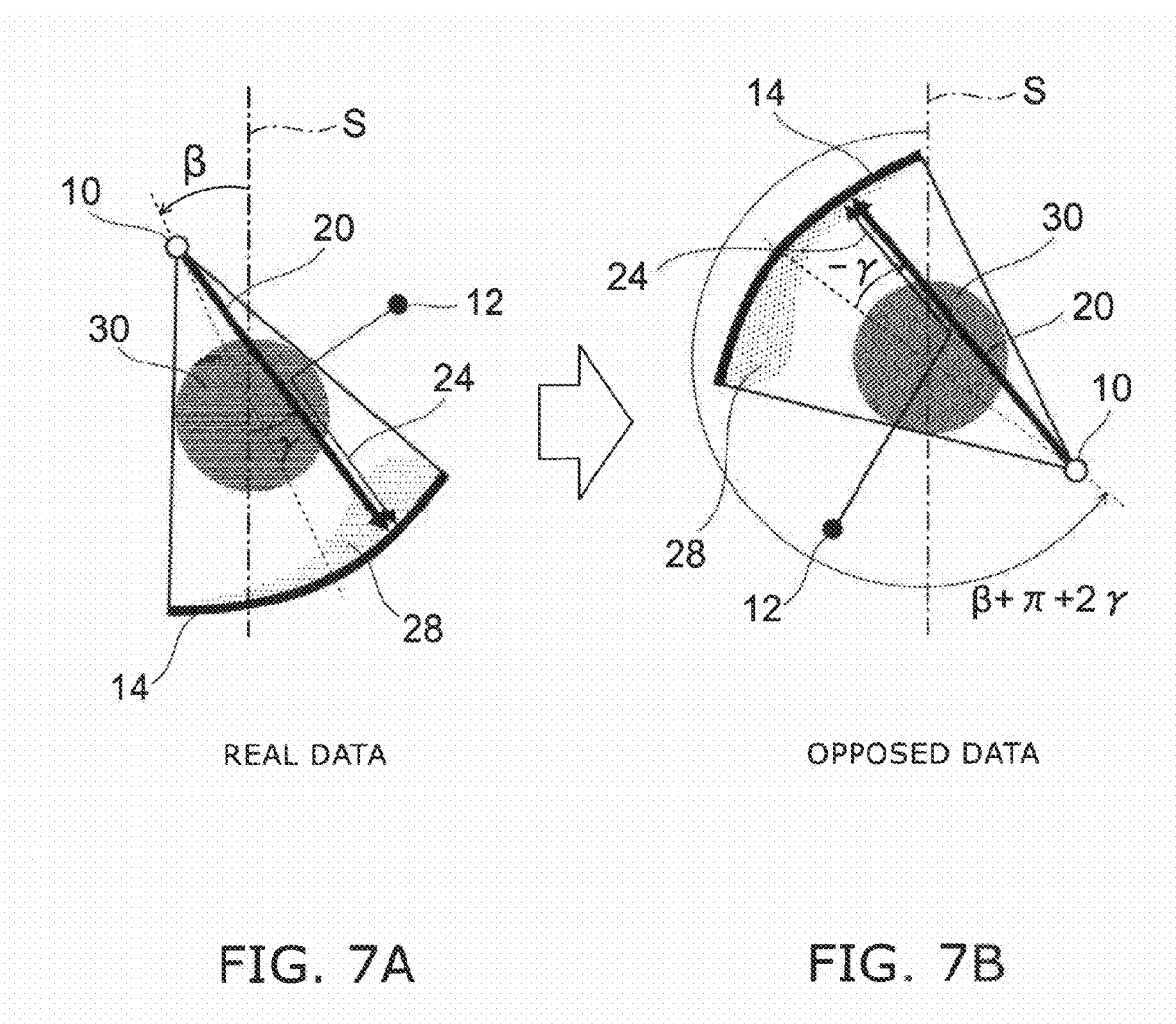
FIGS. 7A and 7B are schematic views describing the method for scaling the scattered ray intensity distribution in the multi bulbs X-ray CT according to the second embodiment of the invention.

FIGS. 7A and 7B are schematic views describing the method for scaling the scattered ray intensity distribution in the multi bulbs X-ray CT according to the embodiment of the invention.

Also in this example, the X-ray source is comprised of the first bulb 10 and the second bulb 12. The X-rays radiated from the first bulb 10 is incident to the subject 30 and the transmission ray 20 passes through the subject 30 to reach the detector 14. Simultaneously, The X-rays radiated from the second bulb 12 is also incident to the subject 30, and the primary scattered ray 24 scattered once in the interior of the subject 30 passes through the subject 30, thereafter reaches the detector 14.

FIG. 7A shows the placement for obtaining the count of the X-ray intensity (real data) incident to the detector 14, and FIG. 7B shows the placement for obtaining the count of the detector 14 (opposed data) in the case where the X-rays pass through the same position of the subject in the opposite direction.

In FIG. 7A, letting a base line passing through the center of the subject 30 be Z, the first bulb 10 is placed in a direction of an angle β viewed from the center of the subject 30 with respect to the base line Z, and the X-rays are radiated from the first bulb 10 in a direction of angle γ in viewing the center of the subject 30. When the angle γ is varied, the intensity distribution of the transmission ray 20 is measured on the detector 14. Moreover, the X-rays radiated from the second bulb 12 is scattered in the interior of the subject 30 to reach the detector 14, and since the transmission path in the subject 30 is shorter in a near side to the second bulb 12 than a far side from the second bulb 12, the measured intensity of the primary scattered ray 24 is stronger in the near side to the second bulb 12 than the far side.

In FIG. 7B, the first bulb 10, the second bulb 12 and the detector 14 are rotated further around the subject 30 by an angle (π+2γ) in comparison with obtaining the real data, so that the X-rays pass through the same position of the subject 30 in the opposite direction. That is, the first bulb 10 is located in the direction of an angle (β+π+2γ) viewed from the center of the subject 30 with respect to the base line Z. Since the X-rays from the first bulb 10 pass through the same position of the subject 30 in the opposite direction, the count on the detector 14 is identical. That is, the difference between the intensity of transmission X-ray from the first bulb 10 included in the real data and the intensity of transmission X-ray from the first bulb 10 included in the opposed data is zero.

On the other hand, the count on the detector 14 of the primary scattered ray 24 scattered once at the same position of the subject 30 after radiation from the second bulb 12 is lower in comparison with the count of obtaining the real data, because the transmission path in the subject 30 is longer. Moreover, the count of the primary scattered ray 24 on the detector 14 is higher on the near side to the second bulb 12. That is, with regard to the intensity of the scattered ray radiated from the second bulb 12, the intensity distribution included in the real data and the intensity distribution included in the opposed data are not identical.

Figure 8:
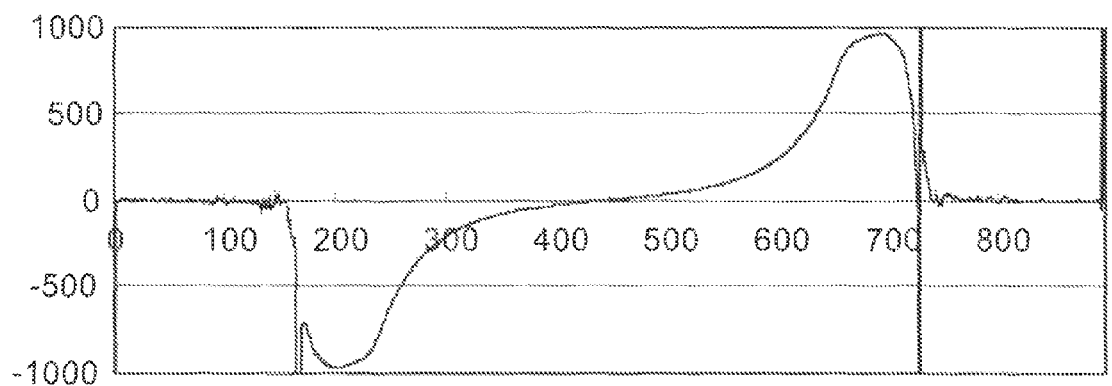
FIG. 8 is a graph view showing a difference profile between the real data and the opposed data of the X-ray intensity.

FIG. 8 is a graph view showing a difference profile between the real data and the opposed data of the X-ray intensity achieved on the detector 14. The subject is assumed to be a cylinder made of water (water cylinder). The difference result reflecting the intensity distribution of the scattered ray from the second bulb 12 is achieved. The horizontal axis represents numbers of the detection channels on the detector 14, and a peak reflecting the intensity distribution on channels apart from the center portion of the detector 14 is achieved.

As described above, the X-ray intensity distribution gives the result reflecting the difference of the intensity distribution of the primary scattered ray 24 between the real data and the opposed data.

As a result, in the multi bulbs X-ray CT, achieving the difference between the real data and the opposed data enables difference data having contribution of the scattered ray to be achieved (S202).

Next, the intensity distribution of the primary scattered ray 24 from the second bulb 12 is calculated to achieve the estimated scattered ray distribution. That is, the distributions of the scattered ray included in the respective real data and the opposed data are estimated.

Here, as one example, estimation of the scattered ray intensity distribution can be performed using the X-ray scattering probability for water.

Figure 9:
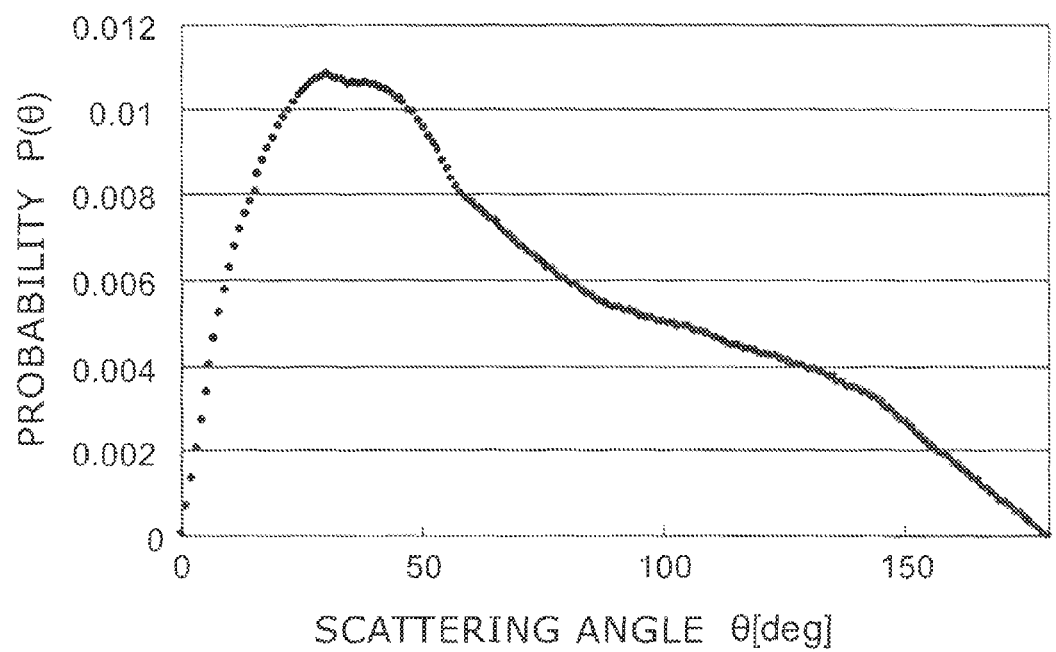
FIG. 9 is a graph view illustrating the scattering probability $P(\theta)$ of X-ray for water.

FIG. 9 is a graph view illustrating the scattering probability $P(\theta)$ of X-ray for water. The scattering probability $P(\theta)$ can be calculated based on an X-ray spectra, a scattering angle and a material of the subject. $\Theta$ is the scattering angle of scattered X-rays with respect to the incident X-rays as described above with reference to FIG. 1.

Figure 10:
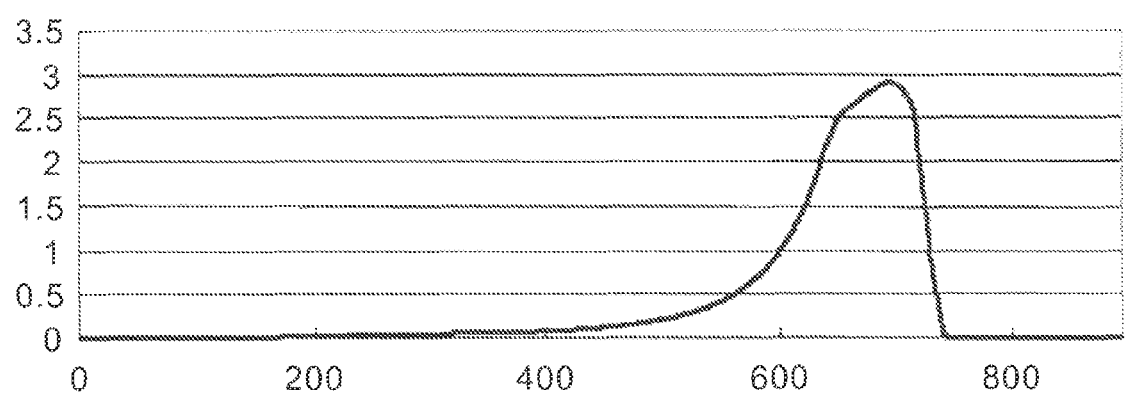
FIG. 10 is a graph view showing the scattering probability $P(\theta)$ of X-ray for water.

FIG. 10 is a graph view showing one example of a profile of the estimated scattered ray from the second bulb 12 for the subject 30 being made of water. Higher intensity is found on the near side to the second bulb 12 on the detector 14, reflecting the difference of the transmission path length in the subject 30.

To estimate the profile of the primary scattered ray, it is available that the intensity Is of the primary scattered ray 24 on the detector 14 is given by the equation (2) using the X-ray intensity Io radiated from the second bulb 12, the transmission path length x of the primary scattered ray 24 passing through the subject 30, the absorption coefficient of the X-ray for water $\mu$, and the scattering probability of the X-ray for water $P(\theta)$. Out of the primary scattered rays 24 radiated from the second bulb 12 to be detected on the same channel on the detector 14, the transmission ray 20 from the first bulb 10 and all primary scattered rays 24 incident to the detector 14 at the same angle are integrated, and thereby the count of the X-ray intensity of the primary scattered ray 24 on the same channel described above is achieved. The count of the intensity distribution of the primary scattered ray 24 on the detector 14 is calculated by varying the angle $\gamma$, and the real data of the estimated scattered ray is achieved.

Furthermore, the count of the primary scattered ray 24 at the alignment of the first bulb 10 and the second bulb 12 rotated by 180° is calculated and the scattered ray included in the opposed data not shown is estimated.

The intensity of the scattered ray intensity distribution increases on the near side to the second bulb 12, therefore the estimated scattered ray distribution produces a difference between the real data and the opposed data. As a result, the difference data can be achieved on the estimated scattered ray (S204).

The estimated scattered ray distribution just shows only relative intensity, therefore scaling is necessary for correcting the count of the X-ray intensity achieved really on the detector 14. For this purpose, estimation is performed on peak value of the difference data between the real data and the opposed data of the count on the detector 14 illustrated in FIG. 8 and on the difference data between the scattered ray included in the real data and the scattered ray included in the opposed data, and scaling of the difference data of the scattered ray is performed based on a ratio of these difference data, for example, peak values.

The scaled profile of the primary scattered ray 24 can be achieved from the scaled difference data of the estimated scattered ray (S206).

Correction of X-ray intensity achieved by the detector 14 using the scaled primary scattered ray intensity distribution enables the cross-sectional image to be reconfigured.

Figure 11A:
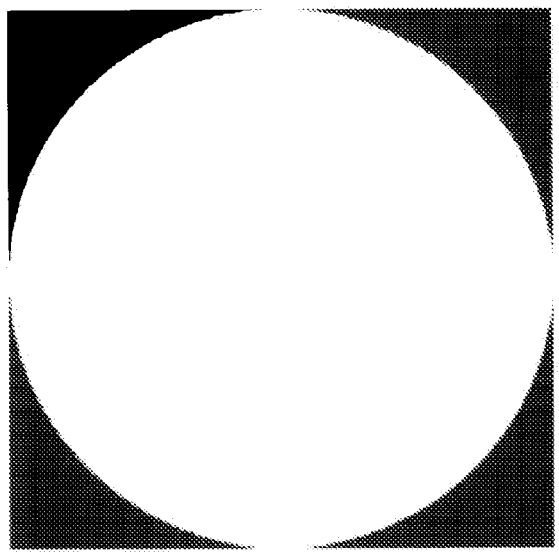
FIGS. 11A to 11C are cross-sectional images showing the correction result of water cylinder simulation data.
Figure 11B:
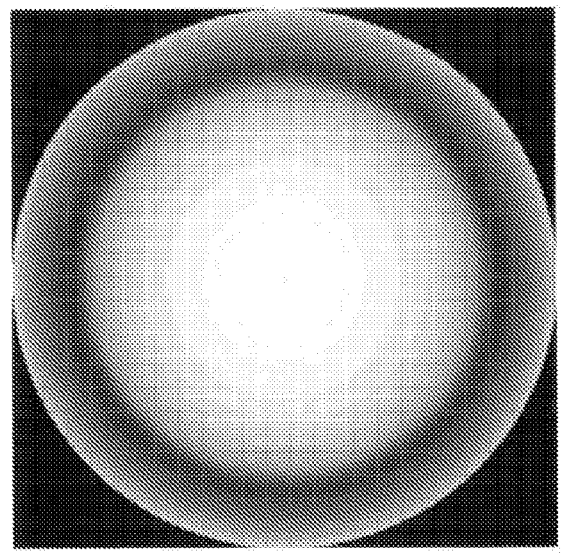
Figure 11C:
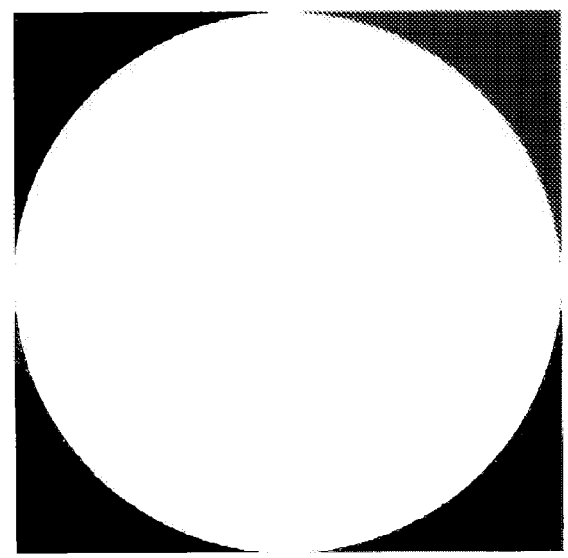

FIGS. 11A to 11C are cross-sectional images showing the correction result of water cylinder simulation data.

The cross-sectional image is achieved by forming the water cylinder using simulation, radiating the X-rays appropriately from the first bulb 10 and the second bulb 12, and performing the scattered ray correction.

FIG. 11A is the cross-sectional image without radiation from the second bulb 12. Since water has a uniform structure, the cross-sectional image does not indicate light and dark or the like.

FIG. 11B is the cross-sectional image including the scattered ray with radiation from the second bulb 12. The image indicates heterogeneous light and dark caused by the scattered ray.

FIG. 11C is the cross-sectional image with the correction of the scattered ray effect from the second bulb 12 using the method of the embodiment. The effect of the primary scattered ray is removed and the cross-sectional image with uniform brightness is achieved.

Next, the X-ray CT apparatus according to the embodiment of the invention will be described.

Figure 12:
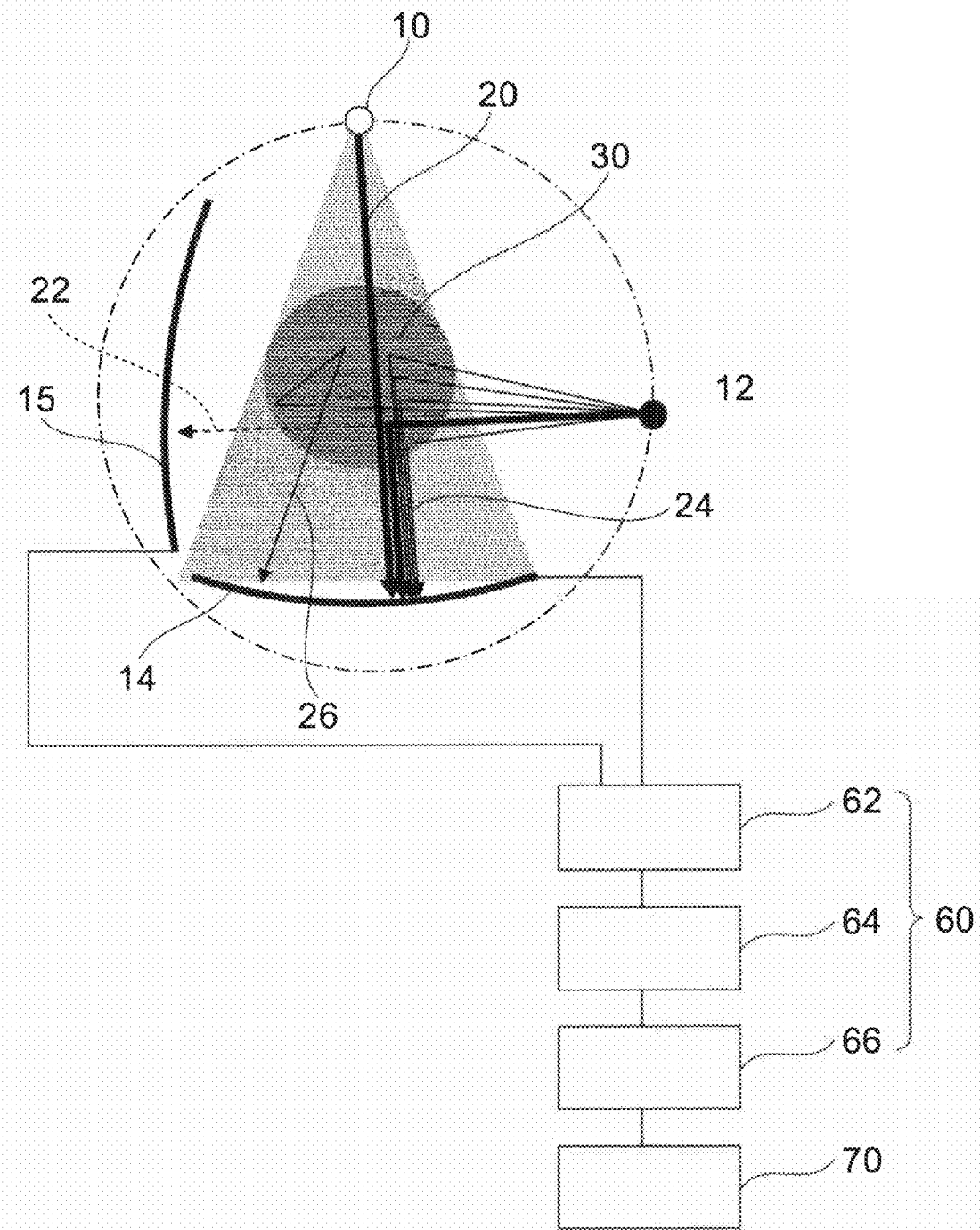
FIG. 12 is a schematic view illustrating the multi bulbs X-ray CT apparatus allowing the scattered ray intensity distribution to be estimated.

FIG. 12 is a schematic view illustrating the multi bulbs X-ray CT apparatus allowing the scattered ray intensity distribution to be estimated.

The X-ray CT apparatus is comprised of the first bulb 10, the second bulb 12, the subject 30, the detectors 14, 15 and a scattered ray calculation section 60 and an image reconfiguration section 70 connected to the detectors 14, 15.

The transmission ray 20 from the first bulb 10 and the multiply scattered ray 26 and the primary scattered ray 24 from the second bulb 12 are incident to the detector 14. The transmission ray 22 from the second bulb 12 and the primary scattered ray from the first bulb 10 are incident to the detector 15. The scattered ray calculation section 60 performs scaling of the scattered ray intensity distribution by the method described above with reference to FIG. 1 to FIG. 12 for the X-ray intensity distribution formed from the transmission ray 20 and the primary scattered ray 24 detected by the detector 14. That is, the scattered ray calculation section 60 has a first calculation section 62, a second calculation section 64 and a third calculation section 66. The first calculation section 62 calculates the path length of the scattered ray passing through the subject. The second calculation section 64 estimates the intensity of the scattered ray on the basis of the path length, the X-ray absorption coefficient of the subject and the scattering probability by the subject. The third calculation section 66 performs scaling of the estimated scattered ray distribution based on the ratio between the peak value of the difference data between the real data and the opposed data of the count on the detectors 14, 15 and the peak value of the difference data achieved by estimating the scattered ray distribution included in the real data and the opposed data, respectively.

On the basis of the scattered ray intensity distribution achieved like this, the X-ray intensity distribution is corrected with regard to the scattered ray component, and the image reconfiguration section 70 forms the cross-sectional image using the correction data.

The primary scattered ray 24 from all X-ray sources (X-ray generation section) including the second bulb 12 is calculated by the scattered ray calculation section 60, thus the scattering of the scattered ray from any X-ray source can be corrected by the calculation. It is also possible that the scattered ray component is calculated by the scattered ray calculation section 60, the X-ray intensity distribution is corrected and the cross-sectional image without degradation of the image quality is reconfigured.

The embodiment of the invention has been described with reference to the examples. However, the invention is not limited to the examples described above. Description is performed about two bulbs, but for example, three bulbs or more may be available.

That is, the invention is not limited to the examples, but can be variously modified without departing from the feature of the invention, and all of these are encompassed within the scope of the invention.

The invention claimed is:

1. A method for scaling a scattered ray intensity distribution in a multi bulbs X-ray CT apparatus configured to irradiate a subject with X-rays from a plurality of X-ray generation sections, respectively and configure a cross-sectional image of the subject by detecting the X-rays passing through the subject, the method comprising:
a first difference being achieved, the first difference being the difference between a real data of a first X-ray intensity achieved by passing of X-rays through the subject, the X-rays being radiated from the plurality of the X-ray generation sections, respectively and an opposed data of a second X-ray intensity achieved by passing of these X-rays through a same position of the subject in an opposite direction,
a second difference between scattered ray intensity included in the real data and scattered ray intensity included in the opposed data being achieved, including:
estimating a first primary scattered ray included in the real data of the first X-ray intensity achieved by passing of the X-rays through the subject, the X-rays being radiated from the plurality of the X-ray generation sections, respectively;
estimating a second primary scattered ray included in the opposed data of the second X-ray intensity achieved by passing of the X-rays through the subject at the same position in an opposite direction, respectively; and
performing scaling of an estimated primary scattered ray intensity distribution on the basis of a ratio between the first difference and the second difference.

2. The method for scaling the scattered ray intensity distribution in the multi bulbs X-ray CT apparatus according to claim 1, wherein the estimated primary scattered ray intensity distribution is scaled on the basis of a ratio between peak values of the first difference and the second difference.

3. The method for scaling the scattered ray intensity distribution according to claim 1, wherein a transmission path of the X-rays passing through the subject is determined.

4. The method for scaling the scattered ray intensity distribution according to claim 1, wherein the estimated primary scattered ray intensity distribution is performed by calculating a path length of the first primary scattered ray and the second primary scattered ray passing through the subject, and by calculating an intensity of the first primary scattered ray and the second primary scattered ray on the basis of the path length, an X-ray absorption coefficient of the subject and an X-ray scattering probability by the subject.

5. The method for scaling the scattered ray intensity distribution according to claim 1, wherein the estimated primary scattered ray intensity distribution is performed by calculating an intensity of the first primary scattered ray and the second primary scattered ray assuming uniformity of a structure of the subject.

6. The method for scaling the scattered ray intensity distribution according to claim 4, wherein the intensity of the first primary scattered ray and the second primary scattered ray in a direction of the path length is integrated.

7. The method for scaling the scattered ray intensity distribution according to claim 6, wherein the intensity of the integrated first primary scattered ray and second primary scattered ray is calculated for all of the path length.

8. The method for scaling the scattered ray intensity distribution according to claim 1, wherein the intensity of the first primary scattered ray and the second primary scattered ray is calculated under approximation of the subject to water.

9. The method for scaling the scattered ray intensity distribution according to claim 4, wherein the X-ray absorption coefficient is an X-ray absorption coefficient for water.

10. The method for scaling the scattered ray intensity distribution according to claim 4, wherein the X-ray scattering probability is an X-ray scattering probability for water.

11. The method for scaling the scattered ray intensity distribution according to claim 1, wherein a shape of the subject is reconfigured from a projection data including the first primary scattered ray and the second primary scattered ray, and a path length in the subject is achieved from the shape.

12. A multi bulbs X-ray CT apparatus comprising:
a plurality of X-ray generation sections configured to generate X-rays;
an X-ray detection section configured to detect the X-rays passing through a subject;
an image reconfiguration section configured to configure a cross-sectional image of the subject on the basis of results detected by the X-ray detection section; and
a scattered ray calculation section configured to estimate a primary scattered ray intensity distribution of the X-rays passing through the subject,
the scattered ray calculation section:
achieving a first difference between a real data of a first X-ray intensity achieved on the X-ray detection section by passing of the X-rays through the subject, the X-rays being radiated from the plurality of the X-ray generation sections and an opposed data of a second X-ray intensity achieved on the X-ray detection section by passing of these X-rays through a same position of the subject in an opposite direction, and achieving a second difference between scattered ray intensity included in the real data and scattered ray intensity included in the opposed data, including:
  estimating a first primary scattered ray included in the real data of the first X-ray intensity achieved by passing of the X-rays through the subject, the X-rays being radiated from the plurality of the X-ray generation sections;

estimating a second primary scattered ray included in the opposed data of the second X-ray intensity achieved by passing of these X-rays through the subject at the same position in the opposite direction;

performing scaling of the estimated primary scattered ray intensity distribution on the basis of a ratio between the first difference and the second difference; and the image reconfiguration section reconfiguring the cross-sectional image by correcting the results detected by the X-ray detection section using the estimated primary scattered ray intensity distribution scaled by the scattered ray calculation section.

13. The multi bulbs X-ray CT apparatus according to claim 12, wherein the estimated primary scattered ray intensity distribution is scaled on the basis of a ratio between peak values of the first difference and the second difference.

14. The multi bulbs X-ray CT apparatus according to claim 12, wherein the scattered ray calculation section calculates an intensity of the first primary scattered ray and the second primary scattered ray assuming uniformity of a structure of the subject.

15. The multi bulbs X-ray CT apparatus according to claim 12, wherein the scattered ray calculation section includes:
  a first calculation section configured to calculate a path length of the first primary scattered ray and the second primary scattered ray passing through the subject;

a second calculation section configured to estimate the primary scattered ray intensity distribution on the basis of the path length, an X-ray absorption coefficient of the subject and an X-ray scattering probability by the subject; and a third calculation section configured to scale the primary scattered ray intensity distribution estimated from the second calculation section on the basis of the ratio between the first difference and the second difference.

16. The multi bulbs X-ray CT apparatus according to claim 12, wherein the X-ray detection section detects the X-rays generated from one of the plurality of X-ray generation sections to pass through the subject, and the first primary scattered ray and the second primary scattered ray.

17. The multi bulbs X-ray CT apparatus according to claim 12, wherein the image reconfiguration section configures the cross-sectional image of the subject by reconfiguring a projection data achieved by rotating one of the plurality of X-ray generation sections and another of the plurality of X-ray generation sections around the subject.

18. The multi bulbs X-ray CT apparatus according to claim 12, wherein the scattered ray calculation section calculates an intensity of the first primary scattered ray and the second primary scattered ray under approximation of the subject to water.

19. The multi bulbs X-ray CT apparatus according to claim 15, wherein the scattered ray calculation section calculates an intensity of the first primary scattered ray and the second primary scattered ray using an X-ray absorption coefficient for water as the X-ray absorption coefficient.

20. The multi bulbs X-ray CT apparatus according to claim 15, wherein the scattered ray calculation section calculates an intensity of the first primary scattered ray and the second primary scattered ray using a scattering probability for water as the scattering probability.

* * * * *